US012379441B2

United States Patent
Maixner (10) Patent No.: US 12,379,441 B2
(45) Date of Patent: Aug. 5, 2025

(54) CIRCUIT ASSEMBLY FOR CORRECTION OF AN INPUT SIGNAL, USE OF THE CIRCUIT ASSEMBLY FOR DETECTION OF A PHYSIOLOGICAL SIGNAL IN A MAGNETIC RESONANCE (MR) SYSTEM

(71) Applicant: Bruker BioSpin GmbH & Co. KG, Ettlingen (DE)

(72) Inventor: Michael Maixner, Bietigheim (DE)

( * ) Notice: Subject to any disclaimer, the term of this patent is extended or adjusted under 35 U.S.C. 154(b) by 0 days.

(21) Appl. No.: 18/432,246

(22) Filed: Feb. 5, 2024

(65) Prior Publication Data

US 2024/0230812 A1 Jul. 11, 2024

(51) Int. Cl.
*G01R 33/565* (2006.01)
*A61B 5/00* (2006.01)
*A61B 5/308* (2021.01)
*H03K 5/1252* (2006.01)

(52) U.S. Cl.
CPC ........ *G01R 33/56509* (2013.01); *A61B 5/308* (2021.01); *A61B 5/7203* (2013.01); *G01R 33/56572* (2013.01); *H03K 5/1252* (2013.01)

(58) Field of Classification Search
CPC ........ G01R 33/56509; G01R 33/56572; A61B 5/308; A61B 5/7203; H03K 5/1252
See application file for complete search history.

(56) References Cited

U.S. PATENT DOCUMENTS

| | | | | |
|---|---|---|---|---|
| 4,204,170 A | * | 5/1980 | Kage | H03K 5/1252 327/552 |
| 4,571,548 A | | 2/1986 | Jordan | |
| 4,795,914 A | * | 1/1989 | Higa | H02J 9/061 307/64 |

(Continued)

FOREIGN PATENT DOCUMENTS

| | | |
|---|---|---|
| DE | 69927328 | 6/2006 |
| DE | 602004012671 | 5/2009 |

(Continued)

OTHER PUBLICATIONS

Wikipedia Sample-and-Hold-Schaltung, https://de.wikipedia.org/wiki/Sample-and-Hold-Schaltun, retrieved Oct. 31, 2022.

*Primary Examiner* — Jung Kim
(74) *Attorney, Agent, or Firm* — Benoît & Côté Inc.

(57) ABSTRACT

A circuit assembly for correction of an input signal including a useful signal and a disturbance signal comprises: a voltage-controlled circuit having at least one voltage-controlled circuit element, an input interface and an output interface, a resistor connected upstream of the voltage-controlled circuit in series with the voltage-controlled circuit, an operational amplifier having a first amplifier input, a second amplifier input and an amplifier output, and a low-pass filter connected between the input interface of the at least one voltage-controlled circuit element and the first amplifier input of the operational amplifier, wherein the output voltage from the operational amplifier is fed back to the low-resistance terminal of the circuit element in that the low-resistance terminal of the at least one voltage-controlled circuit element is electrically connected to the amplifier output of the operational amplifier and to the second amplifier input of the operational amplifier.

12 Claims, 5 Drawing Sheets

(56) References Cited

U.S. PATENT DOCUMENTS

| | | | |
|---|---|---|---|
| 4,811,191 A * | 3/1989 | Miller | G01R 19/22 |
| | | | 327/104 |
| 4,887,609 A | 12/1989 | Cole, Jr. | |
| 6,356,606 B1 | 3/2002 | Hahm | |
| 7,042,287 B2 | 5/2006 | Robinson | |
| 2003/0086507 A1 | 5/2003 | Kim et al. | |
| 2019/0159733 A1 | 5/2019 | Shusterman | |

FOREIGN PATENT DOCUMENTS

| | | |
|---|---|---|
| EP | 2854630 | 7/2017 |
| WO | 2012145285 | 10/2012 |

* cited by examiner

CIRCUIT ASSEMBLY FOR CORRECTION OF AN INPUT SIGNAL, USE OF THE CIRCUIT ASSEMBLY FOR DETECTION OF A PHYSIOLOGICAL SIGNAL IN A MAGNETIC RESONANCE (MR) SYSTEM

BACKGROUND OF THE INVENTION

Field of the Invention

The invention relates to a circuit assembly for correction of an input signal, wherein the input signal at an input interface of the circuit assembly comprises a useful signal and a disturbance signal.

Description of the Related Art

A circuit assembly for correction of an input signal is known from EP 2 854 630 B1 [1].

Vital parameters of living objects, for example ECG and respiration, are monitored i.a. during magnetic resonance measurements. The switching of gradients in the MR apparatus causes disturbance signals here that can be many times greater than the physiological signal of the vital parameter monitoring, and so it is difficult to evaluate the vital parameter data.

In order to suppress disturbances, it is possible to use sample-and-hold circuits [2] in which a disturbance is recognized by a detector circuit in one circuit component and the signal processing chain is interrupted for the period of disturbance in another circuit component. However, it is not possible by this method to immediately eliminate the disruption, and so disturbance peaks persist in the period before the elimination of the disturbance and distort the signal.

DE 699 27 328 T2 discloses a method and an apparatus for limitation of peak values of an input signal. The apparatus and the method isolate peaks of an input signal on the basis of a limiting threshold voltage, produce an extreme signal that constitutes the local extreme of the signal isolated from peaks, filter the extreme signal on the basis of a suitable pulse filter response, in order to create a filter signal, and combine the filter signal with the input signal delayed by a predetermined period of time in order to create a pulse-limited signal.

DE 60 2004 012 671 T2 discloses an amplification system and a method that reduces peak values associated with an input signal and provides, in one or more spectral bands, correction of the signal distortion and of the out-of-band emissions that result from the peak value reduction. The correction signal that eliminates the signal distortion and out-of-band emissions associated with the peak reduction is calculated or derived electronically. The correction signal is combined with the peak value-reduced signal before or after the amplification of the peak value-reduced input signal.

US 2003/0086507 A1 discloses a method of limiting a signal. This involves searching for the highest peak above a threshold value within a first window which is created from a set of sample values of the signal. Thereafter, a threshold-correcting signal for the highest peak found is added on.

US 2019/0159733 A1 discloses a method that enables the recognition and identification of electromagnetic disturbances in a multitude of signals. The system utilizes an adaptable and versatile modular architecture with a series of modules for different filter functions, conditioning functions, processing functions and wireless transmission functions that can be compiled in various configurations for different settings.

EP 2 854 630 B1 [1] discloses a circuit for use in a magnetic resonance (MR) system for reduction of MR interferences in a physiological signal S(f), for example an ECG signal using filters. The circuit from EP 2 854 630 B1 comprises a first summation/subtraction node, a high-pass filter and a second summation/subtraction node. The first summation/subtraction node inputs a first signal and a second signal, where the first signal contains all the disturbance components N(f) produced by the MRT scanner and a physiological signal S(f), and the second signal contains the physiological signal S(f) and an error signal E(f), and combines the second signal with the first signal by subtraction in order to create a difference signal N(f)−E(f). The high-pass filter filters the difference signal N(f)−E(f) from the first summation/subtraction node. The second summation/subtraction node combines the first signal S(f)+N(f) and the filtered signal H(f)*[N(f)−E(f)] from the high-pass filter by subtraction and creates the second signal S(f)+E(f). However, the use of such filters is effective only in the case of small disturbance amplitudes. But since disturbances occur, especially in MR measurements, where differences in amplitude between useful signal and disturbance of up to a factor of 1000 can occur, the method known from [1] is unsuitable for such measurements.

It is an object of the invention to propose a circuit assembly with which disturbances having large disturbance amplitudes can be rapidly and effectively suppressed. In particular, the circuit assembly is to be suitable for suppressing disturbance signals that can arise for example as a result of gradient pulses in an MR apparatus in such a way that the useful signals have good further processability.

SUMMARY OF THE INVENTION

The circuit assembly according to the invention comprises:
- a voltage-controlled circuit having at least one voltage-controlled circuit element, having a first terminal and a low-resistance second terminal,
- a resistor connected upstream of the voltage-controlled circuit in series with the voltage-controlled circuit,
- an operational amplifier having a first amplifier input, a second amplifier input and an amplifier output, and
- a low-pass filter connected between the first terminal of the at least one voltage-controlled circuit element and the first amplifier input of the operational amplifier.

In the circuit assembly according to the invention, the output voltage from the operational amplifier is fed back to the low-resistance terminal of the circuit element of the voltage-controlled circuit element. For this purpose, the low-resistance terminal of the at least one voltage-controlled circuit element is electrically connected to the amplifier output of the operational amplifier and to the second amplifier input (inverting amplifier input) of the operational amplifier. In this way, the disturbance is detected and the disturbance signal is suppressed by means of the same at least one voltage-controlled circuit element. There is no need to filter the disturbance signal out of the signal routed to the operational amplifier. Instead, as soon as a disturbance is detected, the forwarding of the signal to the operational amplifier is stopped and the signal applied to the operational amplifier before the disturbance is output as corrected signal until the disturbance no longer exists.

There is preferably a further electrical resistor connected between the low-resistance terminal of the voltage-controlled circuit and the inverting amplifier input. By means of the further electrical resistor, it is possible to adjust the amplification factor. The further resistance ensures better stability of the circuit assembly.

In order to avoid oscillations, the amplification factor V of the operational amplifier is set to about 1, but to less than 1, especially to 0.9<V<1. For this purpose, the further resistor (resistor between circuit element and amplifier output) chosen has low resistance. The closer the amplification of operational amplifier in association with the rest of the circuit assembly (especially in association with the resistance between circuit element and operational amplifier and the voltage-controlled circuit elements) comes to the value of 1, the better the suppression of disturbance pulses.

The at least one voltage-controlled circuit element preferably has a control input electrically connected to the input interface via a control resistor. If the voltage at the control input of the voltage-controlled circuit element exceeds a threshold, for example owing to a disturbance, the circuit element becomes conductive and prevents the signal pending at the first terminal of the circuit element from being forwarded to the operational amplifier. The voltage at the first terminal of the circuit element is then virtually the same as the voltage at the low-resistance second terminal of the circuit element. This in turn is approximately the voltage applied there before the disturbance.

The voltage-controlled circuit preferably comprises at least one transistor as circuit element. Alternatively, it is also possible to use relays, field-effect transistors (FETs), tubes or analogue circuits as voltage-controlled circuit elements.

In a specific embodiment, the voltage-controlled circuit comprises two voltage-controlled circuit elements of opposite polarity. This enables suppression of both positive and negative disturbance signals. This relates more particularly to circuit assemblies where transistors or FETs are used as voltage-controlled circuit elements. The semiconductors in these circuit elements then also have different doping (NPN+PNP transistor). In that case, one PNP and one NPN transistor are thus used, the bases of which are electrically connected to one another, the emitters of which are electrically connected to one another, and the collectors of which are electrically connected to one another.

A second circuit element can be dispensed with if it is ensured that a switching operation will be triggered at any polarity of the disturbance, for example when an analogue circuit is used as circuit element.

The useful signal may be a physiological signal, especially an ECG signal.

The disturbance signal may be a signal created by an MR imaging scanner, especially by gradient coils.

In a particularly preferred embodiment of the circuit assembly according to the invention, the low-pass filter is an RC circuit, the capacitor of which is at a reference potential. By means of the capacitor of the low-pass filter, the voltage applied without disturbance is stored. The limiting frequency of the RC circuit is dimensioned here such that it is greater than the frequency of the useful signal in order to minimize distortion thereof.

The circuit assembly according to the invention is used to correct an input signal, wherein the input signal at the input interface comprises a useful signal and a disturbance signal.

The circuit assembly according to the invention is more preferably used in a magnetic resonance (MR) system with an MR imaging scanner and an assembly for detection of a physiological signal, in order to reduce disturbance signals caused by the MR imaging scanner.

The centerpiece of the circuit assembly according to the invention is the circuit with the at least one circuit element (preferably two circuit elements) having one resistor connected upstream of the first terminal and one connected downstream of the first terminal of the voltage-controlled circuit element. This simple circuit assembly forms the disturbance detector and simultaneously brings about the elimination of the disturbance. The small number of components and the short pathways for the signals result in only minimal time intervals between disturbance detection and signal pathway. In this way, virtually perfect elimination of the disturbance is possible.

Further advantages of the invention will be apparent from the description and the drawing. It is likewise possible in accordance with the invention for the aforementioned features and those detailed further each to be used alone or in any combinations of two or more. The embodiments detailed and described should not be regarded as an exhaustive enumeration, but instead have illustrative character for the delineation of the invention.

DETAILED DESCRIPTION

Figure 1:
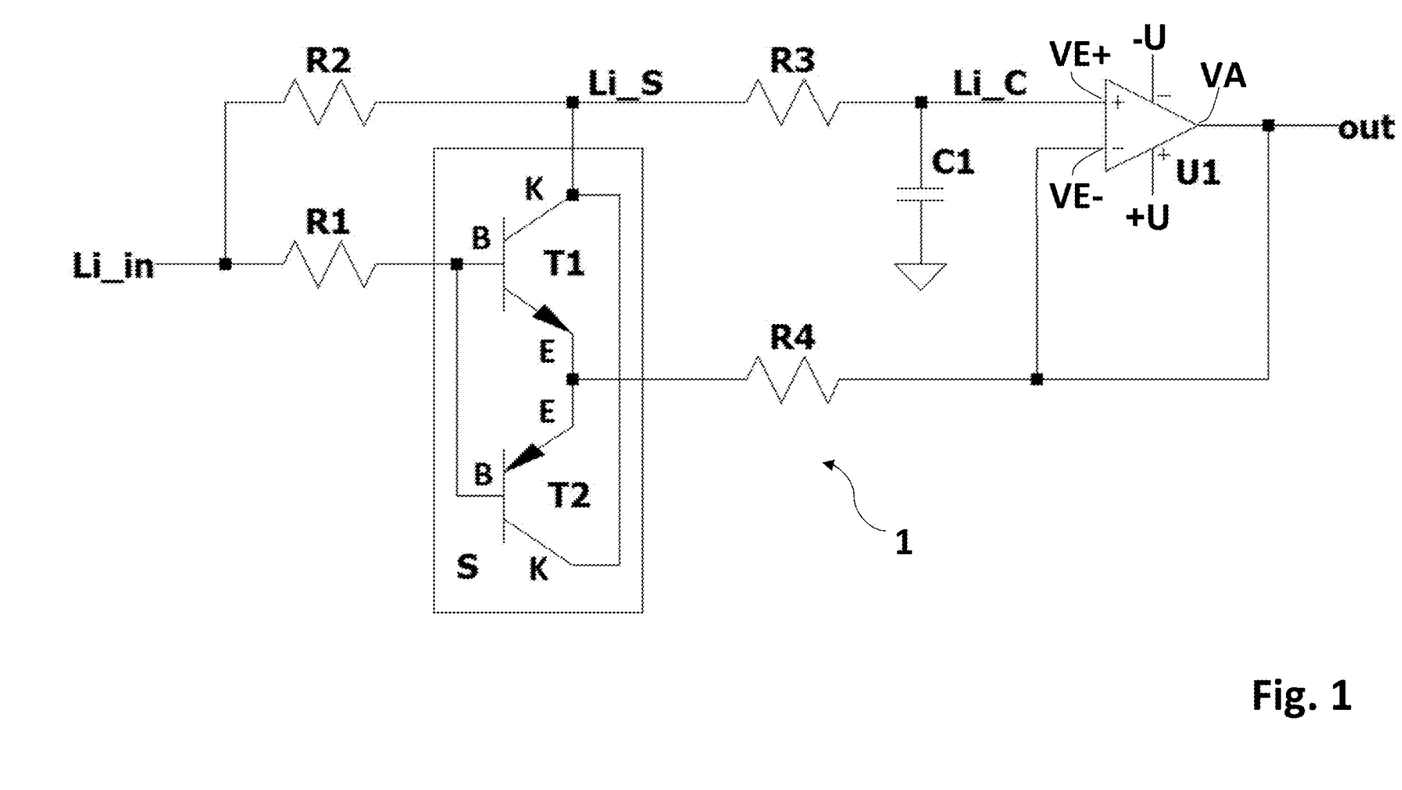
FIG. 1 shows a circuit assembly according to the invention.

FIG. 1 shows a preferred embodiment of the circuit assembly according to the invention. The circuit assembly according to the invention comprises an input interface Li_in to which an input signal V(Ii_in) is applied, a voltage-controlled circuit S, an operational amplifier U1 and an output interface out. The operational amplifier U1 routes the output signal V(Ii_c) to the output interface out. The voltage-controlled circuit S controls the forwarding of the input signal V(Ii_in) to the operational amplifier U1. The output interface out outputs an output signal V(Ii_C).

The voltage-controlled circuit S in the present case comprises two voltage-controlled circuit elements T1, T2 each comprising a first terminal K (in the case of a transistor as circuit element: collector), a low-resistance terminal E (in the case of a transistor as circuit element: emitter) and a control input B (in the case of a transistor as circuit element: base). The voltage-controlled circuit S is disposed between the input interface Li_in and the operational amplifier U1.

The voltage V (Ii_in) is applied via a resistor R2 to the first terminal K of the voltage-controlled circuit elements T1, T2 and via the control resistor R1 to the control inputs B of the voltage-controlled circuit elements T1, T2.

Connected between the interface Li_S at the first terminal K of the voltage-controlled circuit elements T1, T2 and an interface Li_C to the operational amplifier U1 is an RC low-pass filter with a capacitor C1 and a resistor R3.

The operational amplifier U1 comprises a first amplifier input VE+, a second amplifier input VE– and an amplifier output VA.

The low-resistance terminals E of the voltage-controlled circuit elements T1, T2 are electrically connected to the amplifier output VA of the operational amplifier U1. In this way, the output voltage from the operational amplifier U1 is fed back to the low-resistance terminals E of the circuit elements T1, T2. In order to avoid oscillations here, a low-resistance resistor R4 is connected between the low-resistance terminals E of the voltage-controlled circuit elements T1, T2 and the amplifier output VA, and this ensures that the amplification factor of the operational amplifier U1 is always less than the value of 1.

Figure 2:
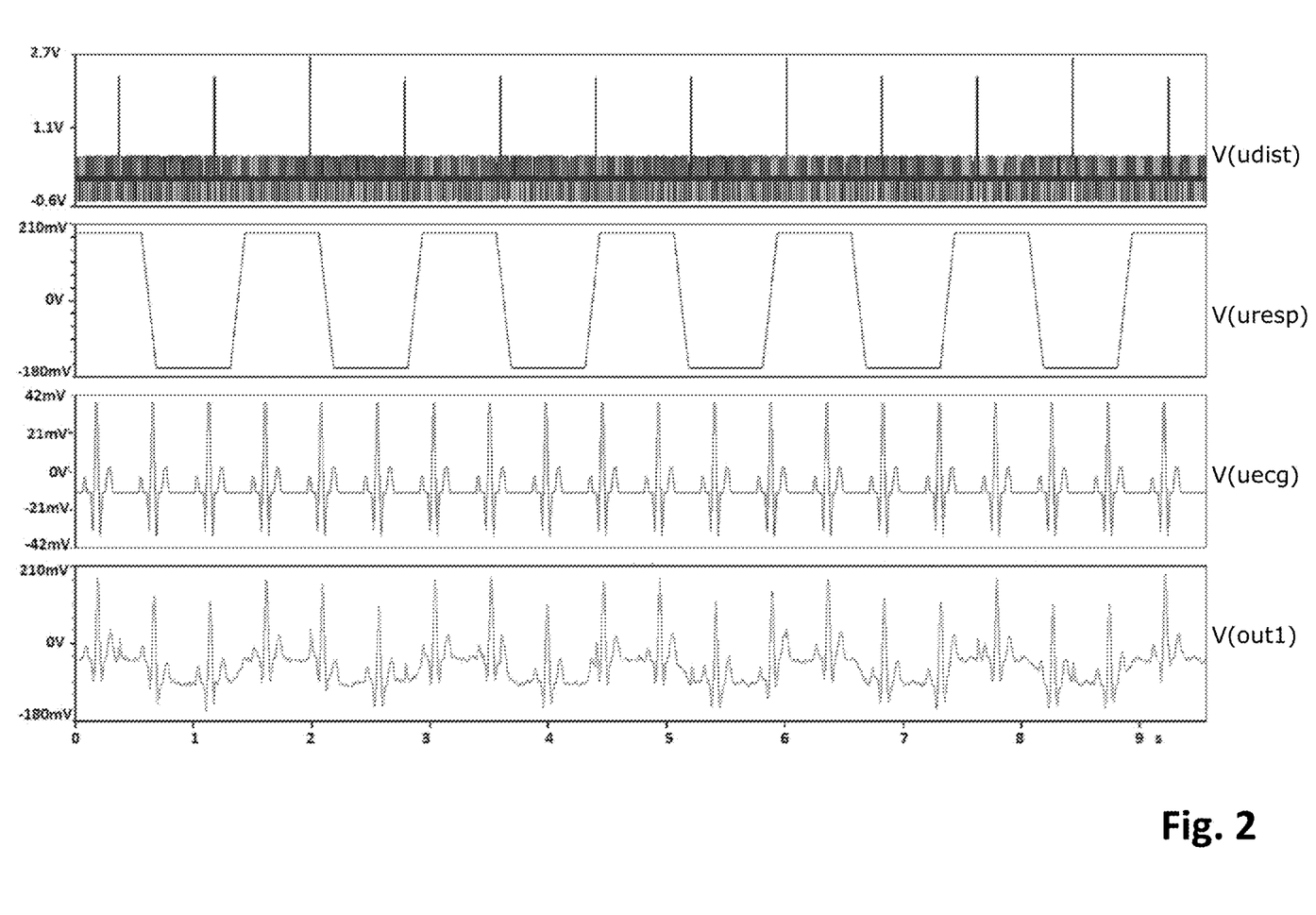
FIG. 2 shows:
the expected signal progression of a disturbance that has been caused by gradient coils of an MR apparatus,
the expected signal progression of respiration monitoring,
the expected signal progression of an ECG, and
the expected signal progression of the superimposition of ECG and respiration monitoring.

FIG. 2 shows, with the upper curve, a progression of a disturbance signal V(udist) of a gradient coil assembly of an MR apparatus. Below that are shown the signal progressions of two physiological signals V(uresp), V(uecg) (here: respiration and ECG) and the superimposition V(out1) of the two physiological signals V(uresp), V(uecg); the superimposition V(out1) of the two physiological signals V(uresp), V(uecg) should be measured as useful signal during NMR measurement. It is clearly apparent that the disturbance signal V(udist) is a whole order of magnitude greater than the highest amplitude of the useful signal V(out1).

Figure 3:
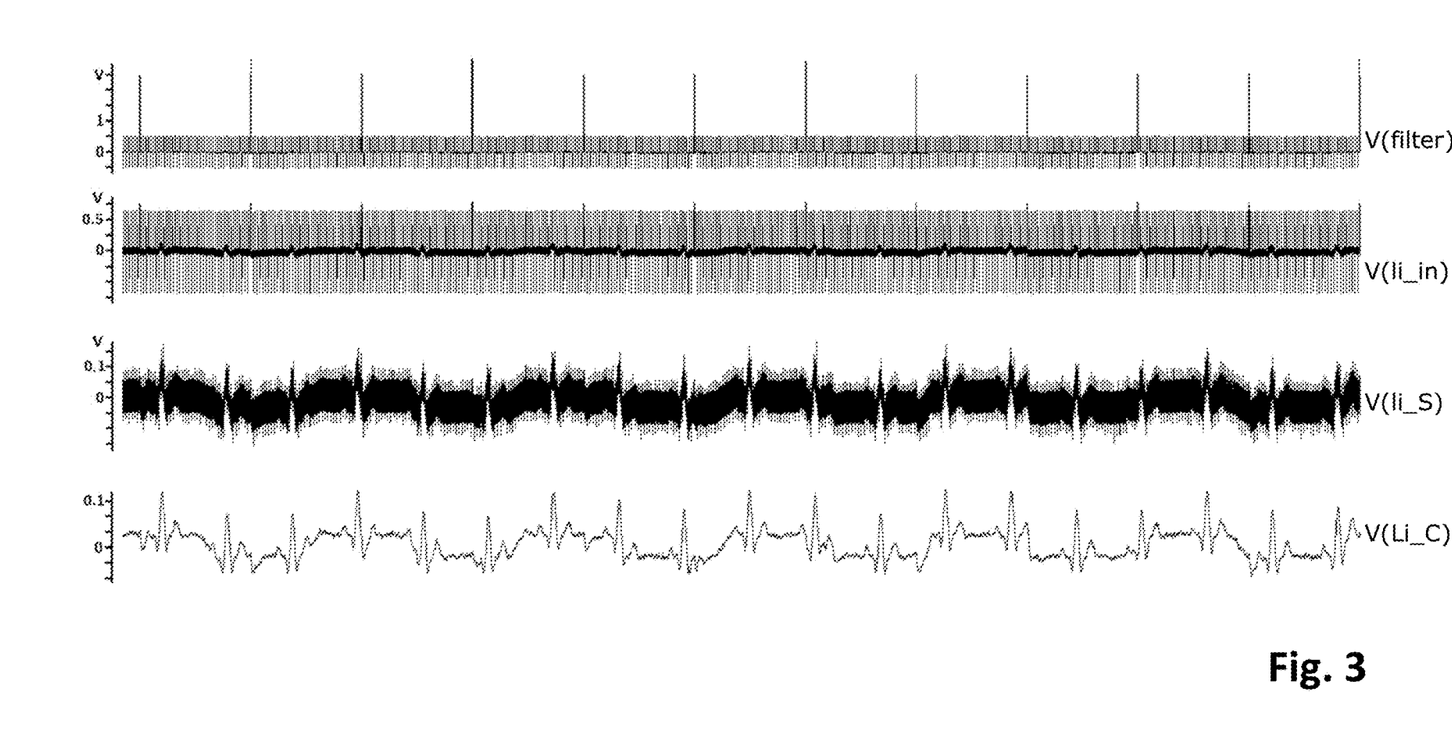
FIG. 3 shows:
the signal progression of a useful signal with a low-frequency and a high-frequency disturbance signal superimposed thereon,
the signal progression of an input signal applied to the input interface,
the signal progression of a signal applied to the interface to the first terminal of the voltage-controlled circuit and
the signal progression of the signal applied to the interface to the operational amplifier.

FIG. 3 shows, with the upper curve, the superimposition V(filter) of a useful signal with a disturbance signal. The superimposition V(filter) is to be processed by means of the circuit assembly 1 according to the invention. For this purpose, the signal V(filter) to be processed can be amplified in multiple stages, such that the useful signal component has a usable intensity (especially about 0.5 V). In order to keep the overloading of the amplifier stages owing to the high amplitude of the disturbance signal within limits here, each amplifier stage is preferably followed by limitation of the amplitude (small signal amplification). This then results in the input signal V(Ii_in) (second signal progression from the top in FIG. 3) for the circuit assembly according to the invention.

In FIG. 1, the circuit elements T1, T2 are configured as transistors. For the on state, generally about 0.7 V is needed between base and emitter of the transistors. In the following, the mode of function of the circuit according to the invention using the example of a circuit having two transistors T1, T2 is described. The use of two transistors enables the processing both of positive and negative useful signals and disturbance signals. For this purpose, the circuit S of the circuit assembly shown in FIG. 1 comprises an NPN transistor T1 and a PNP transistor T2. The two transistors T1, T2 are connected to one another such that the bases, the emitters and the collectors are each electrically connected to one another. The mode of function is applicable analogously to other voltage-controlled circuit elements or to circuits having just one or more than two circuit elements.

By the circuit according to the invention, the input signal V(Ii_in) to be processed is routed via a resistor R1, R2 in each case at the base B and collector K of the transistors T1, T2. At the interface Li_S to the collector K, a processing signal V(Ii_S) is tapped and forwarded with amplification of <1 via the low-pass R3-C1 to the operational amplifier U1 which functions as impedance converter. The limiting frequency of the low-pass R3-C1 will preferably be chosen here such that the highest frequency of the useful signal is attenuated only insignificantly. The output signal from the operational amplifier U1 is sent to the emitter E of the transistors.

Provided that the input signal does not exceed the base-emitter voltage (threshold about 0.6 V), the transistor remains nonconductive and the output signal V(Ii_C) of the impedance converter virtually follows the input voltage of the circuit. For this purpose, the small signal amplification and the voltage at which the circuit S switches to the on state are matched to one another such that the useful signal just fails to switch the circuit S to the on state. If there is no disturbance (i.e. the input signal reflects the useful signal), the input signal V(Ii_in) is then applied to the capacitor C1 of the low-pass filter R3-C1 via the resistors R2 and R3 and to the amplifier output VA of the operational amplifier U1 and is output as output signal V(Ii_C)=V(Ii_in).

If the threshold voltage of the transistors T1, T2 is exceeded (when, for example, the input signal, as well as the useful signal, also includes a disturbance signal greater than the useful signal—V(Ii_in) from FIG. 3), one of the transistors T1, T2 switches to a conductive state and hence brings about, via the resistor R4, a low-resistance connection between the amplifier output VA of the operational amplifier U1 and the low-resistance terminal E of the corresponding transistor T1, T2. The voltage of the input signal V(Ii_in) then drops at the resistor R2 connected in series to the voltage-controlled circuit S. This means that the voltage at the collector K corresponds virtually to the voltage at the emitter E. For the period within which the transistor T1, T2 is conductive, there is no change in the output voltage V(Ii_c) of the impedance converter U1 and the disturbance does not appear in the output VA of the impedance converter U1. The low-pass filter R3-C1 downstream of the circuit S, with the operational amplifier (impedance transducer) U1 downstream in turn, thus ensures intermediate storage of the voltage value of the input signal V(Ii_in) before the occurrence of the disturbance. Thus, in the event of a disturbance, the value stored before the occurrence of the disturbance is output to the operational amplifier U1. This means that the output voltage of the impedance converter U1 does not change during the period in which the circuit element T1, T2 is conductive, and the error does not appear at the output interface out.

The low-pass filter R3-C1 in the present invention does not serve to eliminate the disturbance signal. Instead, the disturbance has already been very substantially suppressed at the interface Li_S to the collector K, since the elimination of the disturbance signal is already brought about by the voltage-controlled circuit. The low-pass filter R3-C1 therefore serves merely to filter the high-frequency components of the useful signal and to store the voltage applied without disturbance. The signal at the interface Li_C is ultimately a useful signal that has been very substantially freed of the disturbances.

Figure 4:
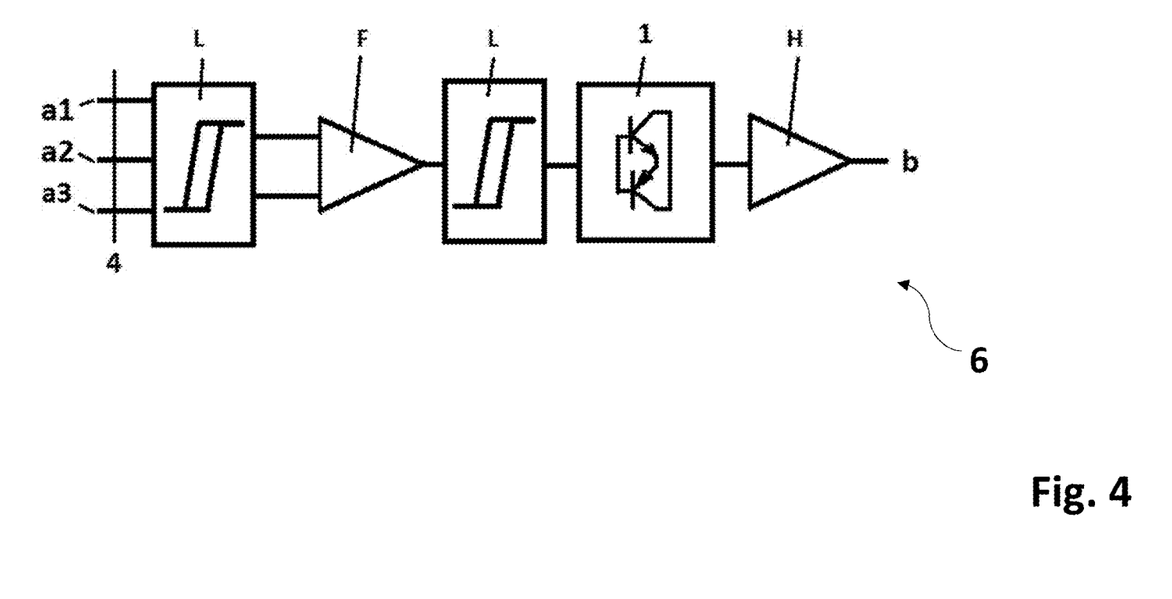
FIG. 4 shows the components of a signal processing device comprising a circuit assembly according to the invention.

FIG. 4 shows the components of a signal processing device 6 that are traversed by a signal detected by electrodes a1, a2, a3 attached on a living measurement object (see FIG. 5) as they are converted to a utilizable useful signal. The signals detected by the electrodes a1, a2, a2 are routed via an interface 4 for detection of physiological signals to a limiter L, an amplifier F and a further limiter L. These serve to achieve the above-described small signal amplification, with limitation of the amplitude before the signal is sent as input signal V(Ii_in) to the circuit assembly 1 according to the invention. The output signal V(Ii_C), after leaving the circuit assembly 1 according to the invention, can be processed further, for example, by means of a further amplifier H.

Figure 5:
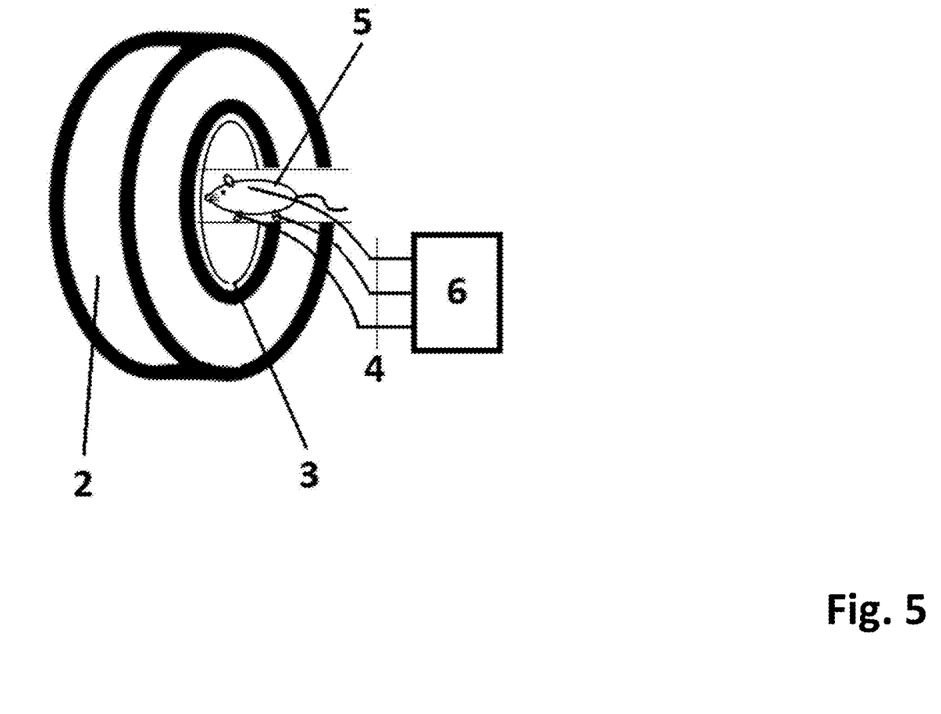
FIG. 5 shows a schematic of a measurement assembly comprising an MR imaging scanner, an assembly for detection of a physiological signal and the signal processing device from FIG. 4.

FIG. 5 shows a measurement system comprising an MR apparatus 2 with gradient coil assembly 3, an interface 4 for detection of physiological signals from a living measurement object 5 and a circuit assembly 1 according to the invention for elimination of disturbance signals caused by the gradient coil assembly 3.

LIST OF REFERENCE NUMERALS

1 circuit assembly
2 MR apparatus
3 gradient coil assembly
4 interface for detection of physiological signals
5 measurement object
6 signal processing device
a1, a2, a3 electrodes
B control input of the circuit element
C1 capacitor of the low-pass filter
E low-resistance second terminal of the circuit element
F, H operational amplifier
K first terminal of the circuit element
L limiter
Li_C interface to the operational amplifier
Li_in input interface
Li_S interface to the first terminal of the voltage-controlled circuit (or of the first terminals of the circuit elements)
out output interface
R1 control resistor (resistor upstream of voltage-controlled circuit)
R2 resistor upstream of low-pass filter
R3 resistor of the low-pass filter
R3-C1 low-pass filter
R4 resistor between low-resistance terminal of the voltage-controlled circuit and second amplifier input of the operational amplifier
S voltage-controlled circuit
T1, T2 voltage-controlled circuit elements
U1 operational amplifier
VA amplifier output
VE+ first amplifier input (noninverting)
VE− second amplifier input (inverting)
V(filter) signal progression of a second physiological signal (ECG)
V(Ii_in) input signal (input voltage)
V(Ii_C) output signal (output voltage)
V(Ii_S) processing signal
V(uresp) signal progression of a first physiological signal (respiration)
V(uecg) signal progression of a second physiological signal (ECG)
V(out1) superimposition of respiration signal and ECG signal
V(udist) disturbance signal from a gradient coil assembly of an MR apparatus

LIST OF LITERATURE

[1] EP 2 854 630 B1
[2] WO 2012/145285 A1

The invention claimed is:

1. A circuit assembly for correction of an input signal, wherein the input signal at an input interface (Li_in) of the circuit assembly comprises a useful signal and a disturbance signal, wherein the circuit assembly comprises:
a voltage-controlled circuit(S) having at least one voltage-controlled circuit element (T1, T2), having a first terminal (K) and a low-resistance second terminal (E), said at least one voltage-controlled circuit element comprising at least one transistor, wherein the first terminal (K) is a collector terminal of the at least one transistor and the second terminal (E) is an emitter terminal of the at least one transistor, the at least one voltage-controlled circuit element (T1, T2) further comprising a control input (B) that is the base terminal of the at least one transistor, the control input (B) being electrically connected to the input interface (Li_in) via a control resistor (R1),
a resistor (R2) connected upstream of the voltage-controlled circuit(S) in series with the voltage-controlled circuit(S), the resistor (R2) electrically connecting the input interface (Li_in) to the first terminal (K) of the at least one transistor,
an operational amplifier (U1) having a first amplifier input (VE+), a second amplifier input (VE−) and an amplifier output (VA), and
a low-pass filter (R3-C1) connected between the first terminal (K) of the at least one voltage-controlled circuit element (T1, T2) and the first amplifier input (VE+) of the operational amplifier (U1),
wherein the output voltage from the operational amplifier (U1) is fed back to the low-resistance terminal (E) of the circuit element (T1, T2) in that the low-resistance terminal (E) of the at least one voltage-controlled circuit element (T1, T2) is electrically connected to the amplifier output (VA) of the operational amplifier (U1) and to the second amplifier input (VE−) of the operational amplifier (U1).

2. The circuit assembly according to claim 1, further comprising a further electrical resistor (R4) that is connected between the low-resistance terminal (E) of the voltage-controlled circuit(S) and the second amplifier input (VE−).

3. The circuit assembly according to claim 1, wherein the operational amplifier (U1) has an amplification factor V with $0.9 < V < 1$.

4. The circuit assembly according to claim 1, wherein the voltage-controlled circuit(S) comprises two voltage-controlled circuit elements (T1, T2) of opposite polarity.

5. The circuit assembly according to claim 1, wherein the useful signal is a physiological signal.

6. The circuit assembly according to claim 5, wherein the physiological signal is an ECG signal.

7. The circuit assembly according to claim 1, wherein the disturbance signal is a signal generated by an MR imaging scanner.

8. The circuit assembly according to claim 7, wherein the disturbance signal is a signal generated by a gradient coil assembly of the MR imaging scanner.

9. The circuit assembly according to claim 1, wherein the low-pass filter (R3-C1) is an RC circuit, the capacitor of which (C1) is at a reference potential.

10. Use of the circuit assembly according to claim 1 for correcting an input signal, wherein the input signal at the input interface (Li_in) comprises a useful signal and a disturbance signal.

11. Use of the circuit assembly according to claim 1 in a magnetic resonance (MR) system having an MR apparatus in order to reduce disturbance signals caused by the MR apparatus.

12. Use of the circuit assembly according to claim 11, wherein the MR apparatus comprises an MR imaging scanner and an assembly for detection of a physiological signal.

* * * * *